(12) United States Patent
Brewster et al.

(10) Patent No.: US 11,197,880 B2
(45) Date of Patent: Dec. 14, 2021

(54) USE OF ERIOCITRIN COMPOSITIONS FOR INCREASING GLP-1 LEVELS

(71) Applicant: INGREDIENTS BY NATURE, LLC, Montclair, CA (US)

(72) Inventors: Robert M. Brewster, West Hills, CA (US); Thais Cesar, Mascotte, FL (US); Carolina Barbosa Ribeiro, Jardim Primavera-Porto Ferreira (BR)

(73) Assignee: INGREDIENTS BY NATURE, LLC, Montclair, CA (US)

( * ) Notice: Subject to any disclaimer, the term of this patent is extended or adjusted under 35 U.S.C. 154(b) by 29 days.

(21) Appl. No.: 16/833,218

(22) Filed: Mar. 27, 2020

(65) Prior Publication Data

US 2020/0306282 A1 Oct. 1, 2020

Related U.S. Application Data

(60) Provisional application No. 62/824,684, filed on Mar. 27, 2019.

(51) Int. Cl.
*A61K 31/7048* (2006.01)
*A61P 3/10* (2006.01)
*A61K 9/00* (2006.01)

(52) U.S. Cl.
CPC ........ *A61K 31/7048* (2013.01); *A61K 9/0053* (2013.01); *A61P 3/10* (2018.01)

(58) Field of Classification Search
None
See application file for complete search history.

(56) References Cited

U.S. PATENT DOCUMENTS

2017/0014439 A1* 1/2017 Brewster .............. A61K 31/353

FOREIGN PATENT DOCUMENTS

JP 200763221 A * 2/2007 ............. A61K 35/78

OTHER PUBLICATIONS

Miyake, Lipids, vol. 33, No. 7, 1998. (Year: 1998).*
Hiramitsu, JP 2007063221, Mar. 15, 2007, machine translation. (Year: 2007).*
Hiramitsu, JP 2007063221, Mar. 15, 2007, CAPLUS English abstract. (Year: 2007).*
CDC, All About Your A1C, internet article, https://www.cdc.gov/diabetes/managing/managing-blood-sugar/a1c.html, Aug. 21, 2018. (Year: 2018).*
Hinnen, Diabetes Spectrum Aug. 2017; 30(3): 202-210. (Year: 2017).*
Avila, J., et al., "The Antidiabetic Mechanisms of Polyphenols Related to Increased Glucagon-Like Peptide-1 (GLP1) and Insulin Signaling," Molecules, vol. 22, No. 6, pp. E903 (2017).
Yaribeygi, H., et al., "Natural compounds with DPP-4 inhibitory effects: Implications for the treatment of diabetes," J. Cell Biochem., vol. 120, Issue 2, pp. (Feb. 18, 2019).
Nyane, N.A., et al., "Metformin-like Antidiabetic, Cardio-protective and Non-glycemic Effects of Naringenin: Molecular and Pharmacological Insights." Eur J. Pharmacol., vol. 803, pp. 103-111 (May 15, 2017).
Xu, L., et al., "Natural products for the treatment of type 2 diabetes mellitus: Pharmacology and mechanisms," Pharmacol Res., pp. 451-564 (Apr. 2018).
Gao, Y., et al., "Recent Progress in Natural Products as DPP-4 Inhibitors," Future Med. Chem., vol. 7, No. 8, pp. 1079-1089 (2015).
Gupta, A., "Citrus Bioflavonoids Dipeptidyl Peptidase-4 Inhibition Compared with Gliptin Antidiabetic Medications," Biochemical and Biophysical Research Communication, vol. 503, Issue 1, pp. 21-25 (Sep. 3, 2018).
clinicaltrials.gov/ct2/show/NCT03215043 (posted on Jul. 12, 2017).
Larsen et el., "Glucagon-Like Peptide 1: A Predictor of Type 2 Diabetes?", Journal of Diabetes Research, vol. 17, Article ID 7583506, 14 pages.
Nauck et al., "Secretion of glucagon-like peptide-1 (GLP-1) in type 2 diabetes: what is up, what is down?", Diabetologia (2011) 54:10-18, 10 pages.

* cited by examiner

*Primary Examiner* — Layla D Berry
(74) *Attorney, Agent, or Firm* — Polsinelli PC; Ron Galant (57) ABSTRACT

Provided herein is a composition comprising eriocitrin, and uses thereof for managing pre-diabetes and diabetes. The composition may be useful for increasing GLP-1 levels.

18 Claims, 5 Drawing Sheets

USE OF ERIOCITRIN COMPOSITIONS FOR INCREASING GLP-1 LEVELS

FIELD OF THE INVENTION

The present invention relates to compositions comprising eriocitrin and their use for managing diabetes and pre-diabetes. The invention also relates to the use of eriocitrin to increase GLP-1 levels.

BACKGROUND OF THE INVENTION

The prevalence of pre-diabetes is increasing worldwide. Almost 500,000 people will have pre-diabetes in 2025. Although the transition from pre-diabetes to diabetes can take years, the American Diabetes Association (ADA) expert panel estimates that up to 70% or prediabetic individuals will eventually progress to diabetes mellitus. In addition, prediabetes is associated with obesity, dyslipidemia, high triglycerides, low HDL-cholesterol and hypertension.

Under current standards of care, preventing pre-diabetes includes lifestyle modifications such as regular physical activity and a balanced diet. Dietary recommendations emphasize vegetables and fruits as sources of polyphenols and dietary fiber. When it is difficult for an individual to make such changes, pharmacological intervention may be necessary. But antidiabetic drugs are associated with increased costs and side effects. Accordingly, there is a need in the art to identify supplements that have favorable effects on glycemic control.

Flavonoids are structurally heterogeneous, polyphenolic compounds that are present at high concentrations in fruits, vegetables, and other plant-derived foods. In particular, ERIOMIN™ is a supplement that contains citrus flavonoids, such as eriocitrin and hesperidin, which are present in lemons, limes and oranges. Some of the inventors have previously shown that experimental mice (C57BL/6J) supplemented with eriocitrin (140 mg/kg/day) exhibit increased total antioxidant capacity and decreased inflammatory markers (IL-6 and MCP-1). Although studies have shown antioxidant and anti-inflammatory activities of flavonoids, there is little information about their activity in metabolic disorders related to pre-diabetes in humans, and about potentially effective doses. Accordingly, there is a further need in the art to identify specific effects of eriocitrin and other plant flavonoids in pre-diabetic and diabetic individuals on metabolic biomarkers, as well as effective doses.

Glycemic control is a tightly coordinated process that requires precise glucose sensing and adequate endocrine response of the pancreas, along with a corresponding response from peripheral tissues. The human GCG gene (2q24.2, Genbank: 2641) codes for proglucagon, a 160 amino acid peptide expressed in the pancreas, gut, and brain, that is post-translationally processed into different peptides according to the organ in question. In L-cells of the small intestine, proglucagon is cleaved into active GLP-1 by prohormone convertase. Serum GLP-1 is present at basal levels, but its release is primarily postprandial in response to nutrient loads. The GLP-1 receptor (GLP-1R) is a 7-transmembrane-spanning heterotrimeric G-protein-coupled receptor (GPCR). It is expressed on various cell types, including pancreatic-cells. There, intracellular signaling takes place through cAMP and other second messengers upon GLP-1 binding, which promotes insulin secretion and gene transcription. GLP-1 and the related glucose-dependent insulinotropic polypeptide (GIP, also known as gastric inhibitory polypeptide) promote insulin secretion and other effects, such as hypothalamic stimulation to induce postprandial satiety. GLP-1 and GIP are both known as incretins, and their effects are considered antidiabetic. Secreted GLP-1 has a very short serum half-life of approximately two minutes, due to extensive hydrolysis by dipeptidyl peptidase-4 (DPP4).

Given the beneficial effects of increased GLP-1 levels on insulin secretion and increased insulin sensitivity, there is a need in the art for agents that are capable of increasing GLP-1 levels.

SUMMARY OF THE INVENTION

Provided herein is a method of increasing GLP-1 levels in a subject in need thereof. The method may comprise administering a composition comprising eriocitrin to the subject. The method may comprise administering about 70-560 mg/d, about 70-280 mg/d, or about 70, 140, 280, or 560 mg/d eriocitrin. The subject may have pre-diabetes, and may have at least one of a hemoglobin A1C level of 5.7%-6.4%, a fasting plasma glucose level of 100-125 mg/dL, and a glucose level of 140-199 mg/dL in a 2-hour post 75 g oral glucose challenge. The subject may have diabetes, and may have at least one of: a fasting plasma glucose level ≥126 mg/dL, a hemoglobin A1C level ≥6.5%, and a glucose level of ≥200 mg/dL in a 2-hour 75 g oral glucose challenge.

The composition may comprise about 50-600 mg eriocitrin, or about 50-200 mg eriocitrin. The composition may also comprise about 70-560, 70-280, 70-140, 70, or 140 mg eriocitrin. The composition may be administered once, twice, or three times daily. The method may comprise administering to the subject 70-560, 70-280, 70-140, 70, or 140 mg/d eriocitrin.

The composition may further comprise at least one of narirutin, hesperidin, and didymin. In particular, the composition may comprise about 70 mg eriocitrin, about 3.6 mg narirutin, about 4.7 mg hesperidin, and about 0.9 mg didymin; about 140 mg eriocitrin, about 7.2 mg narirutin, about 9.4 mg hesperidin, and about 1.8 mg didymin; or about 280 mg eriocitrin, about 14.3 mg narirutin, about 18.8 mg hesperidin, and about 3.6 mg didymin; or about 560 mg eriocitrin, about 28.6 mg narirutin, about 37.6 mg hesperidin, and about 7.3 mg didymin. The composition may be administered once, twice, or three times daily.

The composition may be an oral formulation. The composition may also be administered in combination with another GLP-1 agonist. The method may reverse or induce remission of pre-diabetes or diabetes.

DETAILED DESCRIPTION

The inventors have made the surprising discovery that the eriocitrin compositions described herein increase GLP-1 levels. Without being bound by theory, this may be due to inhibition of DPP4 or promotion of GLP-1 secretion. This effect may be particularly useful for managing symptoms of pre-diabetes and diabetes. The eriocitrin compositions may have particular applications as nutritional supplements or as food additives.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number therebetween with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated. The term "between," when describing the endpoints of a range, means that the endpoints are also included as values of that range, unless stated otherwise.

"About" may mean ±50% of a recited amount. About may also mean ±5% or ±10% of a recited amount.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

2. Flavonoid Composition

Provided herein is a composition comprising eriocitrin. The eriocitrin may be derived, purified, or isolated from a fruit, plant, herb, or other food source. The fruit may be a citrus, such as a lemon. The eriocitrin may have the structure eriodictyol 7-O-B-rutinoside. One particular composition containing eriocitrin described herein is ERIOMIN™.

a. Eriocitrin

The eriocitrin in the composition may be in a complex. The composition may comprise about 50, 55, 60, 65, 70, 75, or 80% wt/wt eriocitrin, or an amount in a range between two of the foregoing values. The composition may also contain eriocitrin as the only flavonoid, so that the flavonoid in the composition is pure or substantially pure eriocitrin. Substantially pure in this context may mean that the flavonoids in the composition are at least about 60, 65, 70, 75, 80, 85, 90, 95, 99.0, 99.1, 99.2, 99.3, 99.4, 99.5, 99.6, 99.7, 99.8, or 99.9% wt/wt eriocitrin.

The composition may comprise about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, or 800 mg eriocitrin, or an amount in a range between two of the foregoing values. In particular, the composition may comprise about 50, 60, 70, 80, 90, 100, 110, 120, 130, 140, 150, 160, 170, 180, 190, or 200 mg eriocitrin, or an amount in a range between two of the foregoing values. The composition may comprise about 70, 140, 280, or 560 mg; or 70-560, 70-280, or 70-140 mg eriocitrin.

b. Flavonoid Combination

The complex may comprise at least one flavonoid other than eriocitrin, which may be one or more of hesperidin, narirutin, and didymin. The composition may comprise about 1, 2, 3, 4, 5, or 6% wt/wt hesperidin, or an amount in a range between two of the foregoing values. The composition may comprise about 5, 6, 7, 8, 9, 10, 11, 12, 13, 14, or 15 mg hesperidin, or an amount in a range between two of the foregoing values. The composition may comprise about 1, 2, 3, 4, 5, or 6% wt/wt narirutin, or an amount in a range between two of the foregoing values. The composition may comprise about 4, 5, 6, 7, 8, 9, 10, 11, or 12 mg narirutin, or an amount in a range between two of the foregoing values. The composition may comprise about 0.5, 1, 2, or 3% wt/wt didymin, or an amount in a range between two of the foregoing values. The composition may comprise about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 mg didymin, or an amount in a range between two of the foregoing values. In particular, the composition may comprise about 70% wt/wt eriocitrin, 3.6% wt/wt narirutin, 4.7% wt/wt hesperidin, and 0.9% wt/wt didymin, and the composition may be referred to as ERIOMIN™. The composition may also comprise about 70 mg eriocitrin, about 3.6 mg narirutin, about 4.7 mg hesperidin, and about 0.9 mg didymin; about 140 mg eriocitrin, 7.2 mg narirutin, 9.4 mg hesperidin, and 1.8 mg didymin; or about 280 mg eriocitrin, 14.32 mg narirutin, 18.8 mg hesperidin, and 3.6 mg didymin; or about 560 mg eriocitrin, 28.6 mg narirutin, 37.6 hesperidin, and 7.2 mg didymin.

c. Additional Agents

The composition may also comprise an additional agent, which may be an omega-3 fatty acid, a plant extract, a coenzyme, a flavonoid, a polymethoxylated flavone (PMF), a limonoid, or a green tea extract. The omega-3 fatty acid may be in an ethyl ester or triglyceride form. The plant extract may be of *Eurycoma longifolia* or Tongat Ali. The coenzyme may be Coenzyme Q10 (CoQ10). The flavonoid may be quercetin dihydrate. The PMF may comprise a hydroxylated polymethyoxylated flavone (HO-PMF). The PMF may be tangeretin, nobiletin, scutellarein, or sinensetin. The limonoid may be citrus-derived.

The additional agent may also be one or more of chromium, cinnamon, diosmin, diosmetin, naringin, naringenin, curcumin, a grapeseed extract, resveratrol, vitamin D, vitamin C, quercetin, and rutin. In particular, the composition may comprise one or more of vitamin C, resveratrol, and a green tea extract. The composition may comprise about 50, 75, 100, 125, 150, 175, 200, 225, 250, 275, 300, 325, 350, 375, 400, 425, 450, 475, or 500 mg of the additional agent, or an amount in a range between two of the foregoing values.

d. Formulation

The composition may be a plant or fruit extract that is directly formulated, such as by encapsulation. The extract may also be used as an intermediate used to make a formulation. The composition may be included in a formulation such as an oral formulation. The formulation may be a self-assembling colloidal delivery system such as the VESISORB® system (Vesifact AG, Zurich, Switzerland), which may be as described in U.S. Patent Publication No. 20060292191, 20050191330, 20040152612, 20030190347, or 20020106390, or U.S. patent application Ser. No. 10/110, 212, the contents of which are incorporated herein by reference.

The composition may be in an oral formulation comprising a tablet, capsule, or lozenge formulated in a conventional manner. The oral formulation may contain one or more conventional excipients including a binding agent, filler, lubricant, disintegrant or wetting agent. The binding agent may be syrup, accacia, gelatin, sorbitol, tragacanth, mucilage of starch or polyvinylpyrrolidone. The filler may be lactose, sugar, microcrystalline cellulose, maize starch, calcium phosphate, or sorbitol. The lubricant may be magnesium stearate, stearic acid, talc, polyethylene glycol, or silica. The disintegrant may be potato starch or sodium starch glycollate. The wetting agent may be sodium lauryl sulfate. Tablets may be coated according to methods well known in the art. The composition may be formulated as a soft gelatin formulation. The soft gelatin may comprise one or more of gelatin, purified water, glycerin, soy lecithin, beeswax, annatto, silicon dioxide, and titanium dioxide.

The composition may also be a liquid formulation such as an aqueous or oily suspension, solution, emulsion, syrup, or elixir. The composition may also be formulated as a dry product for constitution with water or other suitable vehicle before use. Such liquid preparations may contain an additive such as a suspending agent, emulsifying agent, nonaqueous vehicle or preservative. The suspending agent may be sorbitol syrup, methyl cellulose, glucose/sugar syrup, gelatin, hydroxyethylcellulose, carboxymethyl cellulose, aluminum stearate gel, or hydrogenated edible fat. The emulsifying agent may be lecithin, sorbitan monooleate, or acacia. The nonaqueous vehicle may be an edible oil, almond oil, fractionated coconut oil, oily ester, propylene glycol, or ethyl alcohol. The preservative may be methyl or propyl p-hydroxybenzoate or sorbic acid.

The composition may also be formulated as a suppository, which may contain a suppository base such as cocoa butter or glycerides. The composition may also be formulated for inhalation, which may be in a form such as a solution, suspension, or emulsion that may be administered as a dry powder or in the form of an aerosol using a propellant, such as dichlorodifluoromethane or trichlorofluoromethane. The composition may also be formulated in a transdermal formulation comprising an aqueous or nonaqueous vehicle such as a cream, ointment, lotion, paste, medicated plaster, patch, or membrane.

The composition may also be formulated for parenteral administration such as by injection, which may be intraperitoneal, or continuous infusion. Formulations for injection may be in the form of suspensions, solutions, or emulsions in oily or aqueous vehicles, and may contain a formulation agent such as a suspending, stabilizing, or dispersing agent. The composition may also be provided in a powder form for reconstitution with a suitable vehicle including sterile, pyrogen-free water.

The composition may also be formulated as a depot preparation, which may be administered by implantation or by intramuscular injection. The composition may be formulated with suitable polymeric or hydrophobic materials (as an emulsion in an acceptable oil, for example), ion exchange resins, or as sparingly soluble derivatives (as a sparingly soluble salt, for example).

The composition may also be formulated as a liposome preparation. The liposome preparation may comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used. The composition may be intended to target skin conditions. The composition may comprise niosomes. Niosomes are lipid vesicles similar to liposomes, with membranes consisting largely of non-ionic lipids, some forms of which are effective for transporting compounds across the stratum corneum.

e. Nutritional Supplement and Food Additive

The composition may also be used as a food additive, such as in the manufacture of a functional food or beverage. The composition may also be used in a nutritional supplement.

3. Methods of Use

Provided herein is a use of the composition in a method for managing one or more symptoms of pre-diabetes or diabetes in a subject in need thereof, which may comprise administering the composition to the subject. Also provided herein is a method of increasing GLP-1 levels in a subject in need thereof, which may comprise administering the composition to the subject. The composition may promote GLP-1 secretion or increase GLP-1 half-life. The composition may inhibit DPP4. Increasing GLP-1 levels may in turn increase insulin secretion and/or insulin sensitivity. Increasing GLP-1 levels may also increase post-prandial satiety. The composition may also be used to decrease C-peptide or glucagon levels, or increase adiponectin levels. The composition may be used as an adjunct to diet and exercise to improve glycemic control in a subject described herein.

Also provided herein is use of the composition in a method of reversing pre-diabetes or diabetes in a subject in need thereof, which may comprise administering the composition to the subject. The composition may be used to induce remission of pre-diabetes or diabetes in a subject.

The subject may be an animal, which may be a mammal such as a human. The subject may have pre-diabetes. For example, the subject may have impaired fasting glucose (IFG) or impaired glucose tolerance (IGT). The subject may have a hemoglobin A1C level of 5.7%-6.4%, a fasting plasma glucose level of 100-125 mg/dL, or a glucose level of 140-199 mg/dL in a 2-hour post 75 g oral glucose challenge. The subject may have diabetes, and may have a fasting plasma glucose level ≥126 mg/dL, a hemoglobin A1C level ≥6.5%, or a glucose level of ≥200 mg/dL in a 2-hour 75 g oral glucose challenge.

The composition may be used in the foregoing methods in combination with a GLP-1 agonist. The GLP-1 agonist may be liraglutide, dulaglutide, semaglutide, exenatide, sitagliptin, vildagliptin, saxagliptin, albiglutide, or taspoglutide. The eriocitrin composition and GLP-1 agonist may be administered concomitantly, either separately or combined, or sequentially.

A dose of a composition described herein may be administered to the subject, once, twice, three, four, or five times daily. In particular, the dose of eriocitrin administered may be about 50, 70, 100, 140, 150, 200, 280, or 560 mg/d, or an amount in a range between two of the foregoing values. The dose of ERIOMIN administered may be about 100, 200, 400, or 800 mg/d, or an amount in a range between two of the foregoing values. In particular, the dose of ERIOMIN may be 100-200, 100, or 200 mg/d.

The present invention has multiple aspects, illustrated by the following non-limiting examples.

Example 1

Eriodictyol and Eriocitrin Complexes

An eriodictyol complex was extracted from citrus. The extracted eriodictyol complex had the following composition, as measured by high-performance liquid chromatography (HPLC).

TABLE 1

| | |
|---|---|
| Eriocitrin | 0.41 |
| Hesperidin | 1.00 |
| Diosmin | 0.31 |
| Eriodictyol | 91.32 |
| Hesparetin | 3.27 |
| Naringenin | 2.24 |
| Total bioflavonoids | 98.55 |

Figure 1:
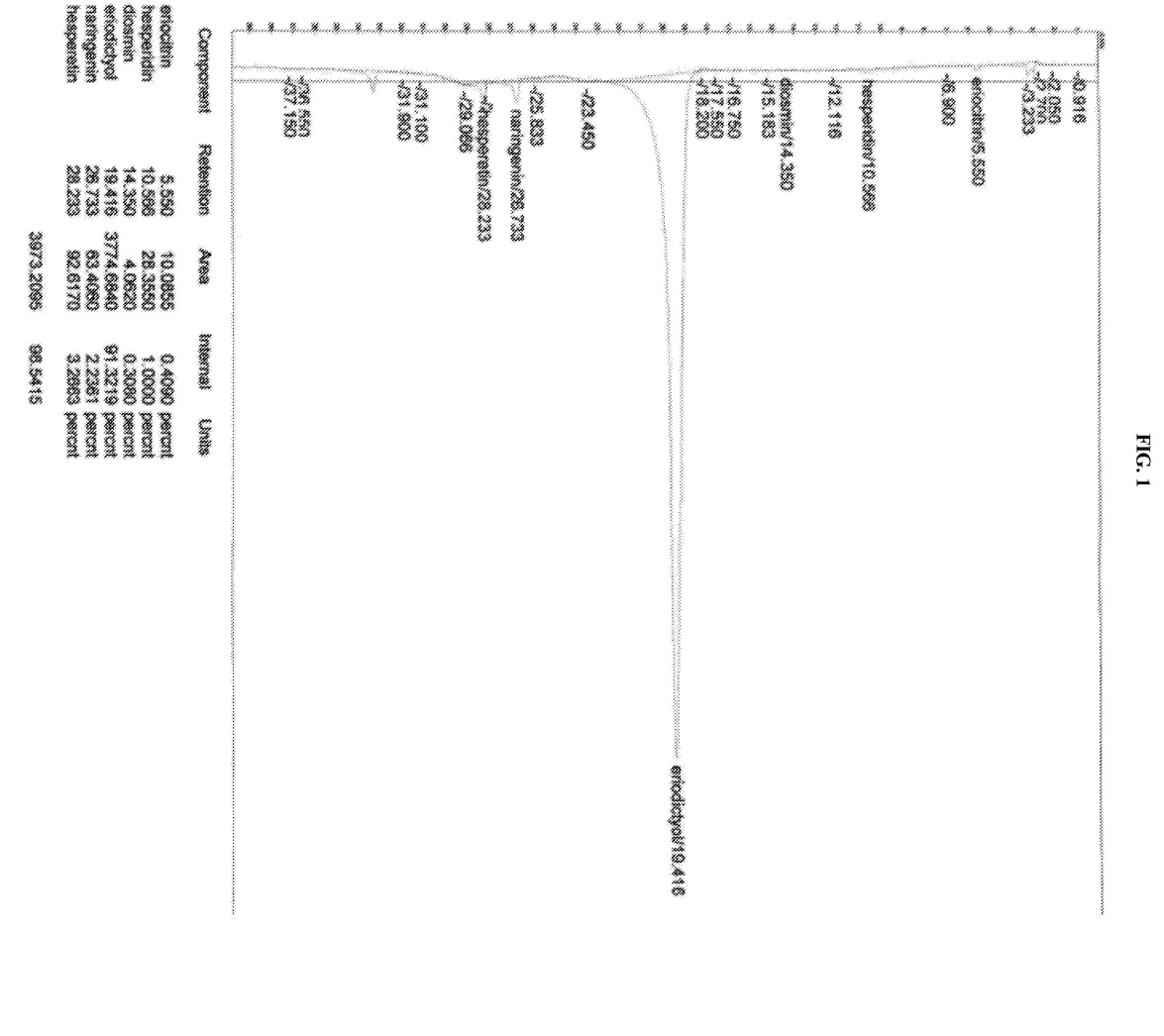
FIG. 1 shows the results of a high-performance liquid chromatography (HPLC) analysis of an eriodictyol complex.

The chromatograph of the analysis of the eriodictyol complex is shown in FIG. 1.

An eriocitrin complex was extracted from citrus. The extracted eriocitrin complex had the following composition, as measured by HPLC.

TABLE 2

| | |
|---|---|
| Eriocitrin | 82.24 |
| Narirutin | 2.47 |
| Hesperidin | 6.52 |
| Didymin | 0.65 |
| Naringenin | 0.11 |
| Hesperetin | 0.03 |
| Other flavonoids | 2.69 |
| Total bioflavonoids | 94.71 |

Example 2

Oxygen Radical Absorbance Capacity Assay

This example describes the anti-oxidant activity of the eriodictyol complex described in Table 1. Anti-oxidant activity was measured using an oxygen radical absorbance capacity assay for food and nutrition ($ORAC_{FN}$). The assay was performed using techniques known in the art, such as those disclosed in Ou, B. et al., J Agric and Food Chem, 2001, 49 (10): 4619-4626; Huang, D. et al., J Agric and Food Chem, 2002, 50 (7): 1815-1821; Ou, B. et al., J Agric and Food Chem, 2002, 50 (10): 2772-2777; Zhang, L. et al., Free Radic. Bio Med, 2007, 43 (suppl. 1): S17; Dubost, N.J. et al., Food Chem, 2007, 105 (2): 727-735; Zhang, L. et al., J Agric and Food Chem, 2009, 57(7): 2661-2667; and U.S. Pat. No. 7,132,296, the contents of all of which are incorporated herein by reference.

The activity of the eriodictyol complex against peroxyl radicals, hydroxyl radicals, peroxynitrite, super oxide anion, and singlet oxygen was measured. The total $ORAC_{FN}$ was also measured. The results are shown in Table 3.

TABLE 3

| Test | Result | Units |
|---|---|---|
| Antioxidant power against peroxyl radicals | 19,643 | µmole TE/gram |
| Antioxidant power against hydroxyl radicals | 49,036 | µmole TE/gram |
| Antioxidant power against peroxynitrite | 1,322 | µmole TE/gram |
| Antioxidant power against super oxide anion | 7,352 | µmole TE/gram |
| Antioxidant power against singlet oxygen | 6,888 | µmole TE/gram |
| Total $ORAC_{FN}$ (sum of above) | 84,241 | µmole TE/gram |

* The acceptable precision of the ORAC assay is <15% relative standard deviation There are five predominant reactive species found in the body: peroxyl radicals, hydroxyl radicals, peroxynitrite, super oxide anion, and singlet oxygen. Total $ORAC_{FN}$ provides a measure of die total antioxidant power of a food/nutrition product against the five predominant reactive species.

Figure 2:
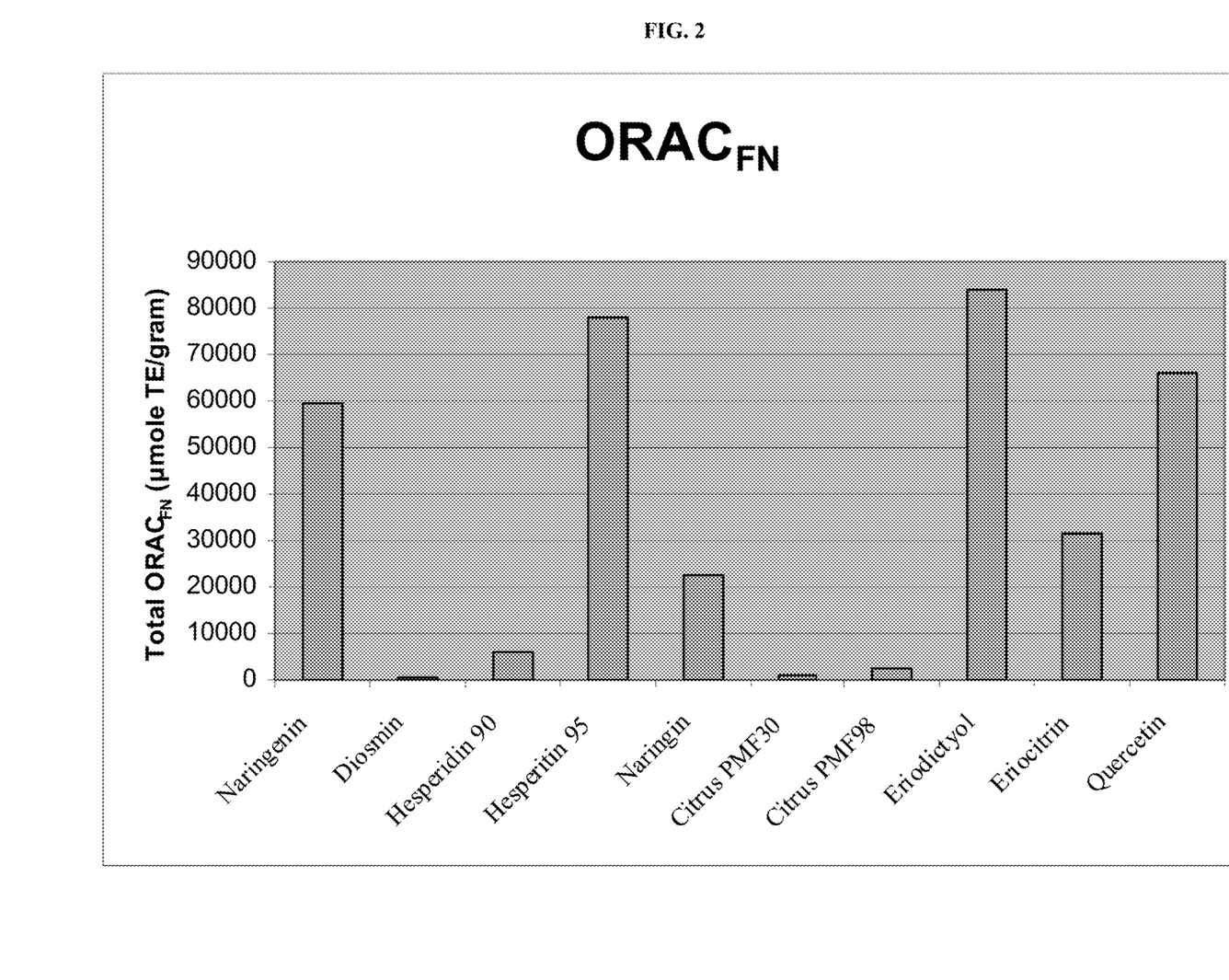
FIG. 2 shows the results of an oxygen radical absorbance capacity assay of the eriodictyol as compared to positive controls.

The activity of the eriodictyol complex was also compared against naringenin, diosmin, hesperidin 90, hesperetin 95, naringin, citrus polymethoxyolated flavone (PMF) 30, citrus PMF98, eriocitrin, and quercetin. The results of the comparison are shown in FIG. 2. The eriodictyol complex exhibited the highest total $ORAC_{FN}$ as compared to all other controls. The results indicate that the eriodictyol complex is a potent anti-oxidant.

Example 3

Inhibition of NFkB

This example demonstrates that the eriodictyol complex has NF-kB inhibitory activity. Activity of the complex was measured using a C2C12 cell line with a NF-kB-luciferase assay system (Affymetrix, Santa Clara, Calif.), and compared to a number of flavonoid controls. The results are shown in Table 4 and in FIG. 3.

TABLE 4

| Description | $EC_{50}$ (µg/ml) |
|---|---|
| Naringenin Lot#99080901 | 32.00 |
| Diosmin Lot#1095100101 | 348.83 |
| Hesperidin 90 Lot#890-19091102-1 | 275.70 |
| Hesperitin 95 Lot#20100101-HESTN | 54.23 |
| Naringin Lot#69591001 | 381.05 |
| Citrus Polymethoxylated Flavones 30 Lot#PMF-67606-30-NT | 96.73 |
| Citrus Polymethoxylated Flavones 98 Lot#39080602 | 48.53 |
| Eriodictyol Lot#ED-20100101 | 1.20 |
| Eriocitrin Lot#20100101-ER | 71.42 |
| Quercetin•2H2O Lot#80807 | 31.49 |

The eriodictyol had the highest level of NF-kB inhibitory activity as compared to all the controls. These results indicate that the eriodictyol complex has potent NF-kB inhibitory activity. A summary of the anti-oxidant and NF-kB inhibitory activity of the eriodictyol complex as compared to controls is shown in Table 5. The amounts shown are relative to quercetin.

TABLE 5

| Description | BL ID | $E_c50$ NF-kB | Compare quercetin | $ORAC_{FN}$ | Compare quercetin |
|---|---|---|---|---|---|
| Naringenin Lot#99080901 | 10-0725 | 32.00 | 0.78 | 59454 | 0.901 |
| Diosmin Lot#1095100101 | 10-0726 | 348.83 | 0.07 | 373 | 0.006 |
| Hesperidin 90 Lot#890-19091102-1 | 10-0727 | 275.70 | 0.09 | 6067 | 0.092 |
| Hesperitin 95 Lot#20100101-HESTN | 10-0728 | 54.23 | 0.46 | 77875 | 1.180 |
| Naringin Lot#69591001 | 10-0729 | 381.05 | 0.07 | 22389 | 0.339 |
| Citrus Polymethoxylated Flavones 30 Lot#PMF-67606-30-NT | 10-0730 | 96.73 | 0.26 | 1039 | 0.016 |
| Citrus Polymethoxylated Flavones 98 Lot#39080602 | 10-0731 | 48.53 | 0.52 | 2396 | 0.036 |
| Eriodictyol Lot#ED-20100101 | 10-0732 | 1.20 | 20.84 | 84241 | 1.276 |
| Eriocitrin Lot#20100101-ER | 10-0733 | 71.42 | 0.35 | 31355 | 0.475 |

This comparison indicates that the eriodictyol complex is 20-times more potent than quercetin in inhibiting NF-kB, and has over 1.2-fold higher anti-oxidant activity than quercetin.

Example 4

Eriocitrin

An eriocitrin complex was extracted from citrus. The extracted complex had the following composition, as analyzed by HPLC on an "as-is" moist basis.

TABLE 6

| BIOFLAVONOIDS | % WT/WT |
|---|---|
| Eriocitrin* | 70.47 |
| Other flavonoid | 3.02 |
| Narirutin | 3.58 |
| Hesperidin | 4.70 |
| Didymin | 0.91 |
| Total bioflavonoids | 82.68 |

Figure 3:
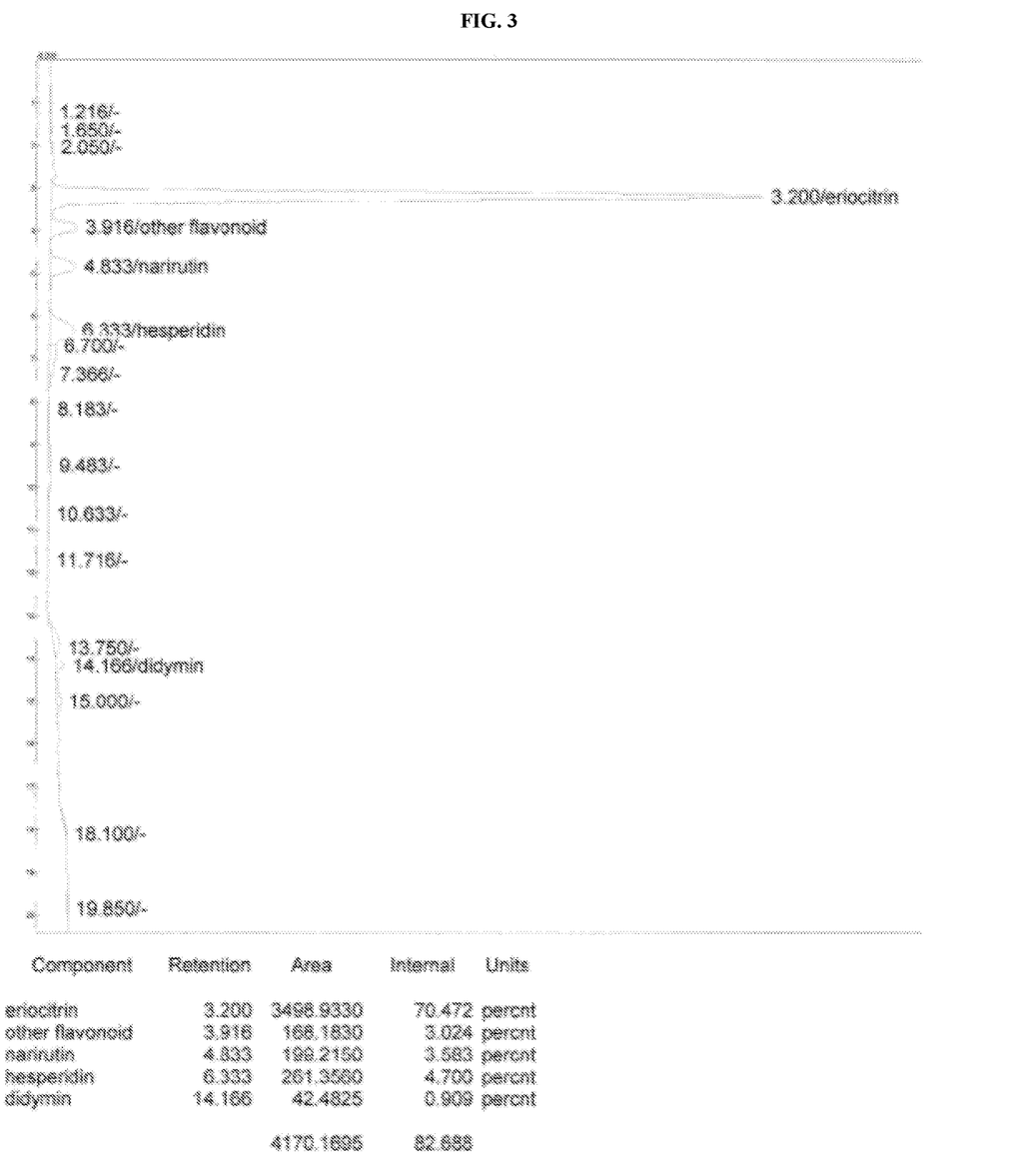
FIG. 3 shows the results of a HPLC analysis of an eriocitrin complex.

The eriocitrin was quantified using a response factor relative to hesperidin, and the eriocitrin content "as hesperidin" would be 62.92%. A chromatograph of the analysis of the eriocitrin complex is shown in FIG. 3.

Example 5

Use of an Eriocitrin Composition for Increasing GLP-1 Levels

This example demonstrates that eriocitrin compositions described herein can be useful for increasing GLP-1 levels.
Methods
Individuals Ninety-six individuals aged 35-60 y and who had pre-diabetes, as identified by at least one of the following criteria: (1) increased fasting glycemia, 6.1 to 7.0 mmol/L (100 to 125 mg/dL), (2) impaired glucose tolerance, 7.8 to 11.1 mmol/L (140-200 mg/dL), and (3) glycated hemoglobin with values between 5.7 and 6.4%, were chosen to participate in this study. Exclusion criteria were based on physiological conditions, such as age (ages >60 years and <35 years were excluded), preconditions such as diseases, and individual behavior, such as use of supplements, drugs, alcohol and physical activity. Sample size was defined based on the primary endpoint, which was lower glycemia after ERIOMIN™, as well as the parallel experimental design (placebo×200 mg×400 mg×800 mg ERIOMIN™), and the significance level of 5% and 80% power of the statistical test.

Trial Design

To evaluate the dose-response to ERIOMIN™, three distinct doses of ERIOMIN™ were selected based on a previous study that showed reduced blood glucose and improved insulin sensitivity in mice supplemented with eriocitrin. A double-blind, randomized, placebo-controlled trial was conducted between November 2017 and February 2018 according to the CONSORT 2010. Pharmacy School UNESP Review Board approved the study (#2119154) and all participants provided written informed consent. The trial was registered at ClinicalTrials.gov (NCT03215043).

A total of 103 eligible individuals were randomly allocated into four groups by an independent investigator, as follows: (1) Placebo: 25 subjects given a daily dose of 400 mg placebo; (2) ERIOMIN™200 mg: 26 subjects given a daily dose of 200 mg ERIOMIN™; (3) ERIOMIN™400 mg: 27 subjects given a daily dose of 400 mg ERIOMIN™; (4) ERIOMIN™ 800 mg: 25 subjects given a daily dose of 800 mg ERIOMIN™. All subjects and the principal investigator remained blind to treatment until all analyzes were completed, and an additional student, not directly involved in the study, was responsible for identifying the vials with the names of the participants.

Supplements Preparation

The intervention product was ERIOMIN™, a supplement of citrus flavonoids provided by INGREDIENTS BY NATURE™, Montclair, Calif. The purity was determined by HPLC. The analyzed ERIOMIN™ contained 70% eriocitrin, 5% hesperidin, 4% naringin and 1% didymin. The placebo was composed of microcrystalline cornstarch. Placebo and ERIOMIN™ were encapsulated in tablets of the same size, shape and color, by a registered pharmacist. Subjects were instructed to consume one capsule after dinner with a glass of water during 12 weeks. Supplements were given to participants every two weeks after randomization.

Dietary Intake and Anthropometric Assessment

In the beginning of the 1st, 4th, 8th and 12th weeks, the following anthropometric parameters were evaluated: body weight (kg), muscle mass (kg), fat mass (kg), body fat (%) (InBody 720, Biospace, Tokyo, Japan) and waist-to-hip ratio was evaluated according to WHO-2008. Blood pressure was measured with digital monitor (ReliOn, HEM-741 CRELN, USA) In addition, registered nutritionists have analyzed usual dietary intake by a 3-day dietary record. Subjects were instructed to maintain their usual diet and physical activity during the total experimental period and the analysis of energy and macronutrient intake was performed using the DIETBOX®, based on the Brazilian Table of Food Composition.

Biochemical Measurements

Overnight fasting blood samples were obtained after $1^{st}$, $4^{th}$, $8^{th}$ and $12^{th}$ weeks of intervention at the São Lucas Clinical Analyzes Laboratory, Araraquara-SP, and blood serum was stored at −80° C. Fasting and postprandial glucose, glycated hemoglobin (HbA1c), total cholesterol, high-density lipoprotein (HDL-cholesterol), triglycerides, Aspartate transaminase (AST), alanine transaminase (ALT), alkaline phosphatase (ALP), and gamma-glutamyl transferase (yGT) were performed by commercial kits (Labtest, Brazil); Low-density lipoprotein (LDL-cholesterol) was calculated. Homeostasis Model Assessment (HOMA-IR) was calculated and the cutoff set at ≥2.71. Lipid peroxidation was assessed by TBARS assay and total antioxidant capacity by radical ABTS•+ assay. Glucagon-like peptide 1 (GLP-1), glucagon, C-peptide, adiponectin, tumor necrosis factor alpha (TNF-α), Interleukin 6 (IL-6) and high-sensitivity C-reactive protein (hsCRP) measurements were performed by LUMINEX MILLIPLEX® (RP3X Scientific, Ribeirao SP, Brazil).

(BMI), muscle mass, fat mass, body fat and waist-to-hip ratio, systolic and diastolic blood pressure, intake of macronutrients, antioxidant capacity and serum lipid peroxidation.

Statistical Analysis

Data are presented as mean±SD. Statistical analysis was performed using SPSS 22 (Statistical Package Social Sciences). One-way ANOVA was used to identify differences between groups in the baseline period. Two-way repeated measures ANOVA followed by Sidak post hoc test were apply to compare changes within and between groups over 12 weeks. The significance was p≤0.05.

Results

Individuals

Figure 4:
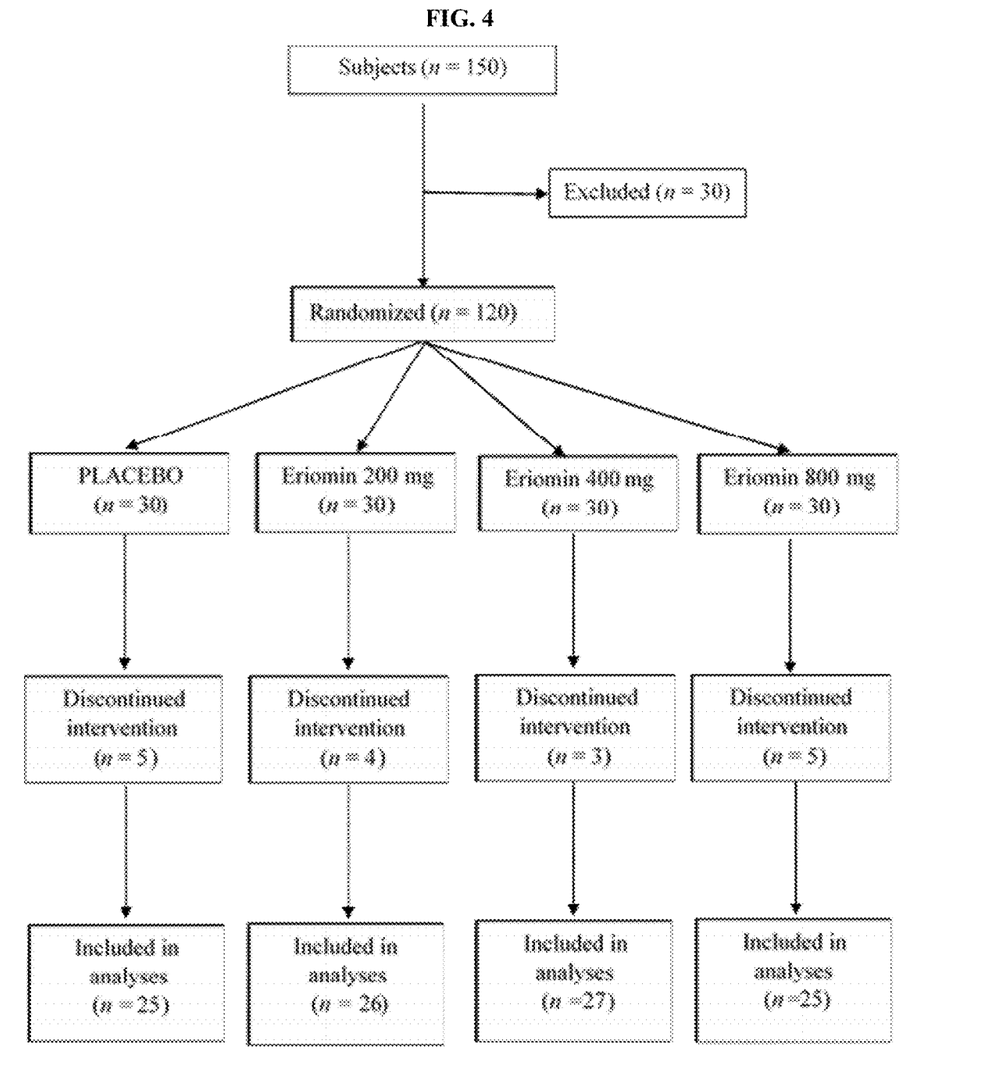
FIG. 4 shows the design of a clinical trial on the effects of an eriocitrin composition disclosed herein.

One hundred and three subjects, 49 men and 54 women, 49±10 y, previously classified as pre-diabetic, were included in this study (FIG. 4). From all volunteers, 41% had altered fasting glycemia, 23% decreased glucose tolerance, and 28% had both conditions. Only 8% had altered glycated hemoglobin (5.7≤HbA1c≤6.4%). The baseline characteristics of all participants were similar among the groups: placebo and 200 mg, 400 mg and 800 mg ERIOMIN™, as shown in Table 7.

TABLE 7

Baseline characteristics of pre-diabetic volunteers submitted to ERIOMIN™ supplementation at 200, 400 or 800 mg/day for 12 weeks

| | | ERIOMIN™ | | |
|---|---|---|---|---|
| Variables | Placebo n = 25 | 200 mg n = 26 | 400 mg n = 27 | 800 mg n = 25 |
| Age | 47 ± 12 | 51 ± 11 | 48 ± 9 | 51 ± 8 |
| Glucose, mg/dL | 104 ± 10 | 104 ± 13 | 104 ± 10 | 103 ± 13 |
| OGTT, mg/dL | 150 ± 17 | 149 ± 21 | 151 ± 19 | 151 ± 19 |
| Insulin, µU/mL | 19.1 ± 6.5 | 19.4 ± 7.2 | 19.3 ± 9.0 | 19.4 ± 6.6 |
| HOMA-IR | 4.70 ± 2.02 | 4.70 ± 1.38 | 4.71 ± 2.26 | 4.71 ± 1.56 |
| HbA1c, % | 5.81 ± 0.50 | 5.82 ± 0.42 | 5.81 ± 0.50 | 5.80 ± 0.51 |
| Total Cholesterol, mg/dL | 193 ± 32 | 184 ± 41 | 190 ± 35 | 184 ± 40 |
| Triglycerides, mg/dL | 146 ± 78 | 152 ± 41 | 151 ± 69 | 162 ± 93 |
| Aspartate transaminase, U/L | 22.1 ± 7.5 | 22.0 ± 7.0 | 23.5 ± 7.2 | 21.5 ± 5.3 |
| Alanine transaminase, U/L | 25.6 ± 15.1 | 24.1 ± 10.5 | 27.1 ± 12.9 | 22.6 ± 7.6 |
| γ Glutamiltransferase, U/L | 42.7 ± 30.8 | 41.0 ± 34.5 | 49.8 ± 58.3 | 34.0 ± 14.4 |
| hsCRP, mg/dL | 0.43 ± 0.36 | 0.44 ± 0.33 | 0.42 ± 0.30 | 0.41 ± 0.42 |
| Glucagon-like peptide-1, pmol/L | 8.48 ± 1.96 | 8.52 ± 2.72 | 8.55 ± 2.75 | 8.57 ± 2.11 |
| Glucagon, pg/mL | 143 ± 19 | 144 ± 23 | 142 ± 19 | 143 ± 14 |
| C-peptide, pg/mL | 2122 ± 636 | 2172 ± 727 | 2163 ± 767 | 2151 ± 624 |
| IL-6, pg/mL | 6.84 ± 4.33 | 6.83 ± 3.12 | 6.82 ± 4.43 | 6.83 ± 4.92 |
| TNF-α, pg/mL | 5.64 ± 1.73 | 5.66 ± 1.91 | 5.67 ± 1.88 | 5.65 ± 1.79 |
| Lipid peroxidation, [MDA] mM | 1.77 ± 0.91 | 1.77 ± 0.58 | 1.78 ± 0.67 | 1.77 ± 0.82 |
| Antioxidant capacity, µM | 1.87 ± 0.03 | 1.88 ± 0.09 | 1.88 ± 0.03 | 1.87 ± 0.09 |
| BMI, kg/m² | 34.2 ± 7.5 | 34.3 ± 7.1 | 33.9 ± 6.6 | 34.0 ± 7.0 |
| Ratio Waist/Hip | 1.06 ± 0.15 | 1.05 ± 0.10 | 1.06 ± 0.11 | 1.06 ± 0.17 |
| Systolic Blood Pressure, mmHg | 135 ± 12 | 133 ± 10 | 133 ± 11 | 134 ± 9 |
| Diastolic Blood Pressure, mmHg | 78.8 ± 15.6 | 80.0 ± 8.0 | 77.8 ± 10.0 | 81.2 ± 6.7 |

OGTT, 2 hours oral glucose tolerance test; HOMA-IR, homeostasis model assessment-insulin resistance; HbA1c, glycated hemoglobin; hsCRP, high-sensitivity C-reactive protein; IL-6: interleukin 6; TNF-α: tumor necrosis factor alpha; BMI, body mass index;
Data are presented as mean ± SD Anova One-Way, p ≤ 0.05

Compliance Assessment

During the intervention, the patients were asked about any discomfort and adverse events. Conformity was assessed by counting unused capsules at each visit. Participants who consumed more than 90% of the provided capsules and completed all evaluations had good compliance and were included in the statistical analysis Primary and Secondary Outcome Measures The primary outcome was serum fasting glucose. The secondary outcome were glucose, HbA1c, insulin, HOMA-IR, total cholesterol, triglycerides, HDL-cholesterol, LDL-cholesterol, ALP, γGT, AST, ALT, GLP-1, glucagon, C-peptide, TNF-α, IL-6, hsCRP, body weight, body mass index Biochemical Markers Fasting blood glucose levels were reduced after ERIOMIN™ treatment in all tested doses. The reductions of −6% were observed at a dose of ERIOMIN™ of 200 mg (p≤0.01), −5% in 400 mg ERIOMIN™ (p≤0.01) and −4% in 800 mg ERIOMIN™ (p=0.041). On the other hand, subjects in the placebo group had an increase in fasting blood glucose levels after twelve weeks (Table 8). In addition, there was a mean reduction of −2% in HbA1c levels in the three groups supplemented with ERIOMIN™ (p≤0.05), whereas placebo showed no change during intervention time (Table 8).

TABLE 8

Biochemical biomarkers of pre-diabetic volunteers submitted to ERIOMIN™ supplementation at 200, 400 or 800 mg/day for 12 weeks.

| Variables | Period week | Placebo | ERIOMIN™ 200 mg | ERIOMIN™ 400 mg | ERIOMIN™ 800 mg |
|---|---|---|---|---|---|
| Glucose, mg/dL | 0 | 104 ± 10 | 104 ± 13 $^a$ | 104 ± 10 $^a$ | 103 ± 13 $^a$ |
|  | 4 | 104 ± 13 $^A$ | 99 ± 11 $^{b,B}$ | 101 ± 12 $^{b,B}$ | 100 ± 12 $^{b,B}$ |
|  | 8 | 103 ± 14 $^A$ | 99 ± 11 $^{b,B}$ | 100 ± 10 $^{b,B}$ | 100 ± 11 $^{b,B}$ |
|  | 12 | 105 ± 16 $^A$ | 98 ± 10 $^{b,B}$ | 99 ± 10 $^{b,B}$ | 99 ± 11 $^{b,B}$ |
|  | $\delta_{(12-0\ wk)}$ | 1.0% | −5.8% | −4.8% −4.8% | −3.9% |
| Insulin, μU/mL | 0 | 19.1 ± 6.5 | 19.4 ± 7.2 | 19.3 ± 9.0 | 19.4 ± 6.6 |
|  | 4 | 19.1 ± 7.6 | 19.1 ± 7.6 | 18.9 ± 10.3 | 19.3 ± 5.8 |
|  | 8 | 19.0 ± 8.6 | 19.1 ± 7.2 | 18.5 ± 7.6 | 19.2 ± 8.0 |
|  | 12 | 19.0 ± 8.9 | 18.2 ± 7.1 | 18.0 ± 8.9 | 19.2 ± 6.3 |
|  | $\delta_{(12-0\ wk)}$ | −0.5% | −6.2% | −6.7% −4.7% | −1.0% |
| HOMA-IR | 0 | 4.70 ± 2.02 | 4.70 ± 1.38 $^a$ | 4.71 ± 2.26 $^a$ | 4.71 ± 1.56 $^a$ |
|  | 4 | 4.70 ± 2.50 | 4.67 ± 1.95 $^a$ | 4.66 ± 2.47 $^a$ | 4.64 ± 1.50 $^a$ |
|  | 8 | 4.68 ± 2.83 | 4.65 ± 1.82 $^a$ | 4.58 ± 1.98 $^a$ | 4.64 ± 1.64 $^a$ |
|  | 12 | 4.74 ± 2.81 $^A$ | 4.31 ± 1.77 $^{b,B}$ | 4.39 ± 1.98 $^{b,B}$ | 4.44 ± 1.69 $^{b,B}$ |
|  | $\delta_{(12-0\ wk)}$ | 0.9% | −8.3% | −6.8% −6.9% | −5.7% |
| HbA1c % | 0 | 5.81 ± 0.50 | 5.82 ± 0.42 $^a$ | 5.81 ± 0.50 $^a$ | 5.80 ± 0.51 $^a$ |
|  | 4 | 5.81 ± 0.51 | 5.80 ± 0.45 $^a$ | 5.81 ± 0.52 $^a$ | 5.78 ± 0.61 $^a$ |
|  | 8 | 5.80 ± 0.51 $^A$ | 5.71 ± 0.45 $^{b,B}$ | 5.72 ± 0.51 $^{b,B}$ | 5.73 ± 0.52 $^{a,A}$ |
|  | 12 | 5.82 ± 0.53 $^a$ | 5.68 ± 0.41 $^{b,B}$ | 5.70 ± 0.42 $^{b,B}$ | 5.70 ± 0.51 $^{b,B}$ |
|  | $\delta_{(12-0\ wk)}$ | 0.2% | −2.4% | −1.9% −2.0% | −7.7% |
| Total Cholesterol, mg/dL | 0 | 193 ± 32 | 184 ± 41 | 190 ± 35 | 184 ± 40 |
|  | 4 | 193 ± 29 | 181 ± 38 | 190 ± 37 | 184 ± 41 |
|  | 8 | 193 ± 24 | 181 ± 40 | 188 ± 30 | 182 ± 40 |
|  | 12 | 195 ± 27 | 181 ± 40 | 187 ± 36 | 182 ± 40 |
|  | $\delta_{(12-0\ wk)}$ | 1.0% | −1.6% | −1.6% −1.4% | −7.7% |
| LDL-cholesterol, mg/dL | 0 | 116 ± 19 | 105 ± 19 | 112 ± 22 | 106 ± 35 |
|  | 4 | 116 ± 17 | 103 ± 24 | 112 ± 30 | 105 ± 37 |
|  | 8 | 116 ± 23 | 103 ± 27 | 110 ± 23 | 103 ± 29 |
|  | 12 | 117 ± 23 | 103 ± 26 | 110 ± 23 | 103 ± 25 |
|  | $\delta_{12-0\ wk}$ | 0.9% | −1.9% | −1.8% −2.2% | −2.8% |
| HDL-cholesterol, mg/dL | 0 | 47.3 ± 11.3 | 46.3 ± 10.9 | 46.6 ± 7.91 | 46.0 ± 10.9 |
|  | 4 | 47.4 ± 10.0 | 45.5 ± 9.96 | 45.5 ± 6.81 | 45.7 ± 9.91 |
|  | 8 | 47.4 ± 11.9 | 45.5 ± 9.36 | 45.1 ± 8.07 | 44.1 ± 10.7 |
|  | 12 | 47.6 ± 10.7 | 45.5 ± 10.6 | 45.1 ± 8.41 | 44.0 ± 10.7 |
|  | $\delta_{(12-0\ wk)}$ | 0.6% | −1.7% | −3.2% −3.1% | −4.3% |
| Triglycerides, mg/dL | 0 | 146 ± 78 | 152 ± 41 | 151 ± 69 | 162 ± 93 |
|  | 4 | 145 ± 88 | 158 ± 51 | 143 ± 60 | 153 ± 80 |
|  | 8 | 148 ± 77 | 144 ± 61 | 149 ± 60 | 152 ± 75 |
|  | 12 | 150 ± 81 | 144 ± 42 | 144 ± 74 | 153 ± 65 |
|  | $\delta_{(12-0\ wk)}$ | 2.7% | −5.3% | −4.6% −5.2% | −5.6% |

Two-way repeated measures ANOVA followed by Sidak test among groups (placebo, 200, 400 and 800 mg) over 12-wk intervention period; p ≤ 0.05. Different letters (a, b) indicate a difference within the group, and different uppercase letters (A, B) indicate a difference between groups.

All volunteers had insulin resistance at the beginning, during, and at the end of the experiment (HOMA-IR≥2.71), but there was a reduction of −8% after intervention with 200 mg of ERIOMIN™ (p=0.037), −7% with 400 mg (p=0.043) and −6% with 800 mg (p=0.042) (Table 8). These results were mainly due to the reduction of blood glucose, because no significant changes were detected in insulin levels (p>0.05). Regarding blood lipids, there was no reduction in total cholesterol, LDL-cholesterol, HDL-cholesterol and triglycerides during and at the end of the experimental period, although the patients did not present high levels of these parameters (Table 8).

Metabolic Markers

The glucose tolerance (OGTT) showed abnormal glucose metabolism at baseline, which is compatible with pre-diabetes. ERIOMIN™ supplementation improved 2-hours blood glucose, with a reduction at the following doses of ERIOMIN™: −7% with 200 mg (p=0.042), and 400 mg (p=0.030) and, −6% with 800 mg (p=0.010) after 12 weeks of treatment (Table 9).

Levels of blood plasma GLP-1 increased 15% for all tested doses of ERIOMIN™: 200, 400, and 800 mg (p<0.001). After intervention, Eriomin supplementation also promoted an average reduction of −6.5% of glucagon (p<0.001) and −5% of C-peptide levels (p<0.001). No change was observed in the placebo group during treatment (Table 9).

TABLE 9

Metabolic and inflammatory biomarkers of pre-diabetic volunteers submitted to ERIOMIN™ supplementation at 200, 400 or 800 mg/day for 12 weeks

| Variables | Period week | Placebo | ERIOMIN™ 200 mg | ERIOMIN™ 400 mg | ERIOMIN™ 800 mg |
|---|---|---|---|---|---|
| OGTT, mg/dL | 0 | 150 ± 17 | 149 ± 21 $^a$ | 151 ± 19 $^a$ | 151 ± 19 $^a$ |
|  | 12 | 151 ± 22 $^A$ | 139 ± 19 $^{b,B}$ | 140 ± 18 $^{b,B}$ | 141 ± 17 $^{b,B}$ |
|  | $\delta_{(12-0\,wk)}$ | −0.7% | −6.7% | −7.3% −6.9% | −6.6% |
| Glucagon, pg/mL | 0 | 143 ± 19 | 144 ± 23 $^a$ | 142 ± 19 $^a$ | 143 ± 14 $^a$ |
|  | 12 | 142 ± 20 $^A$ | 134 ± 21 $^{b,B}$ | 135 ± 19 $^{b,B}$ | 132 ± 14 $^{b,B}$ |
|  | $\delta_{(12-0\,wk)}$ | −0.7% | −6.9% | −4.9% −6.5% | −7.7% |
| C-peptide, pg/mL | 0 | 2122 ± 636 | 2172 ± 727 $^a$ | 2163 ± 767 $^a$ | 2151 ± 624 $^a$ |
|  | 12 | 2106 ± 675 $^A$ | 2047 ± 613 $^{b,B}$ | 2055 ± 803 $^{b,B}$ | 2046 ± 648 $^{b,B}$ |
|  | $\delta_{(12-0\,wk)}$ | −0.8% | −5.8% | −5.0% −5.2% | −4.9% |
| GLP-1, rmol/L | 0 | 8.48 ± 1.96 | 8.52 ± 2.72 $^a$ | 8.55 ±2.75 $^a$ | 8.57 ± 2.11 $^a$ |
|  | 12 | 8.50 ± 1.96 $^A$ | 9.85 ± 2.68 $^{b,B}$ | 9.80 ± 1.95 $^{b,B}$ | 9.89 ± 2.15 $^{b,B}$ |
|  | $\delta_{(12-0\,wk)}$ | 0.2% | 75.6% | 14.6% 15.2% | 15.4% |
| hsCRP, mg/dL | 0 | 0.43 ± 0.36 | 0.44 ± 0.33 $^a$ | 0.42 ± 0.30 $^a$ | 0.41 ± 0.42 $^a$ |
|  | 12 | 0.43 ± 0.41 $^A$ | 0.38 ± 0.25 $^{b,B}$ | 0.39 ± 0.34 $^{b,B}$ | 0.35 ± 0.30 $^{b,B}$ |
|  | $\delta_{(12-0\,wk)}$ | 0.0% | −13.6% | −7.1% −11.8% | −14.6% |
| IL-6, pg/mL | 0 | 6.84 ± 4.33 | 6.83 ± 3.12 $^a$ | 6.82 ± 4.43 $^a$ | 6.83 ± 4.92 $^a$ |
|  | 12 | 6.82 ± 4.61 $^A$ | 5.89 ± 2.23 $^{b,B}$ | 5.84 ± 3.04 $^{b,B}$ | 6.03 ± 3.80 $^{b,B}$ |
|  | $\delta_{(12-0\,wk)}$ | −0.3% | −13.8% | −14.4% −13.3% | −77.7% |
| TNF-α, pg/mL | 0 | 5.64 ± 1.73 | 5.66 ± 1.91 $^a$ | 5.67 ± 1.88 $^a$ | 5.65 ± 1.79 $^a$ |
|  | 12 | 5.63 ± 2.03 $^A$ | 4.98 ± 1.59 $^{b,B}$ | 5.06 ± 1.63 $^{b,B}$ | 5.02 ± 1.96 $^{b,B}$ |
|  | $\delta_{(12-0\,wk)}$ | −0.2% | −12.0% | −10.8% −11.3% | −11.2% |
| Adiponectin, μg/mL | 0 | 18.4 ± 5.6 | 18.7 ± 5.7 $^a$ | 17.9 ± 7.5 $^a$ | 18.1 ± 7.6 $^a$ |
|  | 12 | 18.7 ± 5.3 $^A$ | 22.2 ± 6.6 $^{b,B}$ | 21.8 ± 8.9 $^{b,B}$ | 21.1 ± 6.6 $^{b,B}$ |
|  | $\delta_{(12-0\,wk)}$ | 1.6% | 18.7% | 21.8% 19.0% | 16.6% |
| Lipid peroxidation, [MDA] mM | 0 | 1.77 ± 0.91 | 1.77 ± 0.58 $^a$ | 1.78 ± 0.67 $^a$ | 1.77 ± 0.82 $^a$ |
|  | 12 | 1.76 ± 0.94 $^A$ | 1.33 ± 0.67 $^{b,B}$ | 1.53 ± 0.86 $^{b,B}$ | 1.54 ± 0.84 $^{b,B}$ |
|  | $\delta_{(12-0\,wk)}$ | −0.6% | −24.9% | −14.0% −17.3% | −13.0% |
| Antioxidant capacity, μM | 0 | 1.87 ± 0.03 | 1.88 ± 0.09 $^a$ | 1.88 ± 0.03 $^a$ | 1.87 ± 0.09 $^a$ |
|  | 12 | 1.88 ± 0.03 $^A$ | 1.99 ± 0.04 $^{b,B}$ | 1.99 ± 0.03 $^{b,B}$ | 1.98 ± 0.03 $^{b,B}$ |
|  | $\delta_{(12-0\,wk)}$ | 0.5% | 5.9% | 5.9% 5.7% | 5.3% |

Two-way repeated measures ANOVA followed by Sidak test among groups (placebo, 200, 400 and 800 mg) over 12-wk intervention period; $p \leq 0.05$. Different letters (a, b) indicate a difference within the group, and different uppercase letters (A, B) indicate a difference between groups.

Clinical Reversal of Pre-Diabetic Condition

Figure 5:
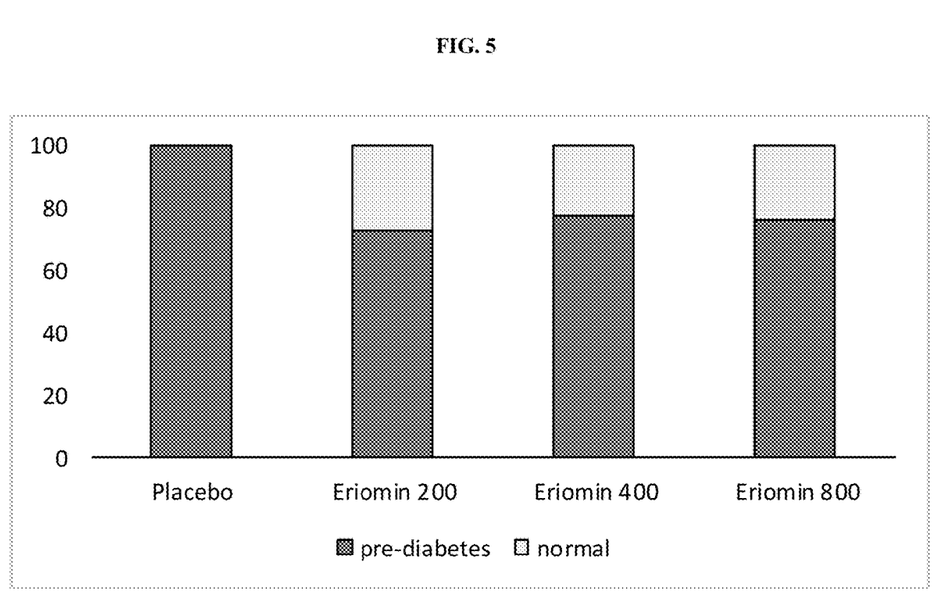
FIG. 5 shows the percentage of pre-diabetic individuals after eriocitrin composition supplementation at 200, 400 or 800 mg/day for 12 weeks.

After 12 weeks, 27% of subjects supplemented with ERIOMIN™ 200, 22% with ERIOMIN™ 400 mg and 24% with ERIOMIN™ 800 reversed pre-diabetes to the normal condition (euglycemia). The placebo group maintained the same number of pre-diabetic individuals (FIG. 5).

Discussion

This study evaluated the efficacy of ERIOMIN™ in the management of hyperglycemia and metabolic parameters, and its contribution to the reversal of the pre-diabetes state in a short time interval. After 12 weeks of ERIOMIN™ supplementation with 200, 400 or 800 mg per day there was a significant decrease in fasting glycemia, impaired glucose tolerance, HOMA-IR, HbA1c, glucagon, C-peptide, hsCRP, IL-6 and TNF-α. In contrast, there were increases in the blood levels of GLP-1, adiponectin and antioxidant capacity.

Under ERIOMIN™ supplementation, a −5% reduction in glycemic levels and a −7% reduction in the glucose tolerance test occurred. Serum HbA1c and insulin resistance, as measured by HOMA-IR, reduced by −2% and −7%, respectively. These findings were clinically relevant because after treatment with ERIOMIN™ 24% of patients reversed the pre-diabetic clinical condition for normal glycemia and/or lower glucose intolerance.

In pre-diabetic humans it has been reported an impairment of serum GLP-1, knowing as an incretin secreted by intestinal L cells after carbohydrate intake. GLP-1 is involved in the regulation of glucose metabolism, stimulating insulin secretion and inhibiting glucagon secretion, thereby lowering plasma glucose levels. In this study, all doses of ERIOMIN™ promoted a 15% increase in GLP-1 levels and a −6% reduction in glucagon levels which was presumably may be associated with improved hyperglycemia in the pre-diabetic volunteers. The eriocitrin in ERIOMIN™ may inhibit dipeptidil peptidase 4 (DPP-4) by increasing the half-life of GLP-1, thereby improving insulin secretion and glucose uptake.

Another relevant marker for pre-diabetes condition is the low level of adiponectin, an adipokine that plays a crucial role in insulin sensitivity and regulation of glucose metabolism, and is considered a risk factor for cardiovascular disease. In contrast, citrus flavonoids positively regulate adiponectin transcription in adipocytes and increase their levels in patients with myocardial infarction. These data corroborate findings showing supplementation increased serum adiponectin levels by 18% in pre-diabetic subjects after 12 weeks of treatment, and reduced by −5% C-peptide concentration, a marker of beta cell function that allows differentiation between type 1 and type 2 in the prognosis of diabetes.

In conclusion, this study showed that short-term intervention with ERIOMIN™, at doses of 200, 400 or 800 mg/d, benefited glycemic control, lowered the systemic inflammation and oxidative stress, and reversed the pre-diabetic condition in 24% of 385 total patients evaluated. This study also showed that an eriocitrin composition can increase GLP-1 levels, reduce glucagon levels, increase adiponectin levels, and reduce C-peptide levels.

The invention claimed is:

1. A method of increasing GLP-1 levels in a subject in need thereof, comprising administering a composition comprising eriocitrin to the subject.

2. The method of claim 1, wherein the subject has pre-diabetes or diabetes.

3. The method of claim 2, wherein the subject has at least one of: a hemoglobin A1C level of 5.7%-6.4%, a fasting plasma glucose level of 100-125 mg/dL, and a glucose level of 140-199 mg/dL in a 2-hour post 75 g oral glucose challenge.

4. The method of claim 2, wherein the subject has at least one of:
a fasting plasma glucose level ≥126 mg/dL, a hemoglobin A1C level ≥6.5%, and a glucose level of ≥200 mg/dL in a 2-hour 75 g oral glucose challenge.

5. The method of claim 1, wherein the composition comprises about 50-600 mg eriocitrin.

6. The method of claim 5, wherein the composition comprises 50-200 mg eriocitrin.

7. The method of claim 1, wherein about 50-600 mg/d eriocitrin is administered to the subject.

8. The method of claim 7, wherein about 50-200 mg/d eriocitrin is administered to the subject.

9. The method of claim 8, wherein about 100-200 mg/d eriocitrin is administered to the subject.

10. The method of claim 8, wherein about 70-140 mg/d eriocitrin is administered to the subject.

11. The method of claim 10, wherein about 140 mg/d eriocitrin is administered to the subject.

12. The method of claim 10, wherein about 70 mg/d eriocitrin is administered to the subject.

13. The method of claim 1, wherein the composition further comprises at least one of narirutin, hesperidin, and didymin.

14. The method of claim 13, wherein the composition comprises about 70 mg eriocitrin, about 3.6 mg narirutin, about 4.7 mg hesperidin, and about 0.9 mg didymin; about 140 mg eriocitrin, about 7.2 mg narirutin, about 9.4 mg hesperidin, and about 1.8 mg didymin; or about 280 mg eriocitrin, about 14.3 mg narirutin, about 18.8 mg hesperidin, and about 3.6 mg didymin; or about 560 mg eriocitrin, about 28.6 mg narirutin, about 37.6 mg hesperidin, and about 7.3 mg didymin.

15. The method of claim 14, wherein the composition is administered to the subject once, twice, or three times daily.

16. The method of claim 1, wherein the composition is an oral formulation.

17. The method of claim 1, wherein the composition is administered in combination with another GLP-1 agonist.

18. The method of claim 2, wherein the method reverses or induces remission of the pre-diabetes or diabetes.

* * * * *